United States Patent
van der Greef

(10) Patent No.: US 6,743,364 B2
(45) Date of Patent: Jun. 1, 2004

(54) METHOD AND SYSTEM FOR IDENTIFYING AND QUANTIFYING CHEMICAL COMPONENTS OF A MIXTURE

(75) Inventor: Jan van der Greef, Driebergen-Rijsenburg (NL)

(73) Assignee: Nederlandse Organisatie voor Toegepast-Natuurwetenschappelijk Onderzoek TNO, Delft (NL)

( * ) Notice: Subject to any disclaimer, the term of this patent is extended or adjusted under 35 U.S.C. 154(b) by 313 days.

(21) Appl. No.: 09/920,993

(22) Filed: Aug. 2, 2001

(65) Prior Publication Data

US 2002/0053545 A1 May 9, 2002

(30) Foreign Application Priority Data

Aug. 3, 2000 (NL) .............................................. 1015875
Aug. 28, 2000 (NL) .............................................. 1016034

(51) Int. Cl.$^7$ ............................................. B01D 15/08
(52) U.S. Cl. ..................... 210/656; 210/198.2; 250/282; 702/19; 702/22
(58) Field of Search ................................ 210/635, 656, 210/659, 198.2; 250/282; 702/19, 22

(56) References Cited

U.S. PATENT DOCUMENTS

| | | | |
|---|---|---|---|
| 5,644,503 A | * | 7/1997 | Ito et al. .......................... 702/22 |
| 5,672,869 A | | 9/1997 | Windig et al. ............... 250/282 |
| 5,910,655 A | | 6/1999 | Skilling ....................... 250/282 |
| 6,393,368 B1 | * | 5/2002 | Ito et al. .......................... 702/22 |
| 6,560,542 B1 | * | 5/2003 | Mandell et al. ................ 702/19 |

FOREIGN PATENT DOCUMENTS

| | | | | |
|---|---|---|---|---|
| WO | WO 99/05591 A3 | 2/1999 | .................. | 702/22 |
| WO | WO 99/05591 A2 | 2/1999 | .................. | 702/22 |

OTHER PUBLICATIONS

Windig, et al., "A Noise and Background Reduction Method for Component Detection in Liquid Chromatography/Mass Spectrometry," *Analytical Chemistry*, vol. 68, No. 20 (Oct. 1996) pp. 3602–3606.

Zhang et al., "Enhancement of the Effective Resolution of Mass Spectra of High–Mass Biomolecules by Maximum Entropy–Based Deconvolution to Eliminate the Isotopic Natural Abundance Distribution," Journal of American Society for Mass Spectrometry (1997) pp. 659–670.

* cited by examiner

*Primary Examiner*—Ernest G. Therkorn
(74) *Attorney, Agent, or Firm*—Testa, Hurwitz & Thibeault, LLP

(57) ABSTRACT

Method and system for processing and evaluating data from combination chromatographic and mass spectrometric data. The methods and system comprise data smoothing and determination of an quality factor for a chromatogram of a data set based on a determined entropy value. In one embodiment, the methods and system further comprise data baseline correction prior to entropy value determination. In a further embodiment, a correlation is determined between chromatograms processed according to the invention and one or more chromatograms of one or more data sets. Preferably, said correlation is performed using a multivariate analysis.

11 Claims, 13 Drawing Sheets

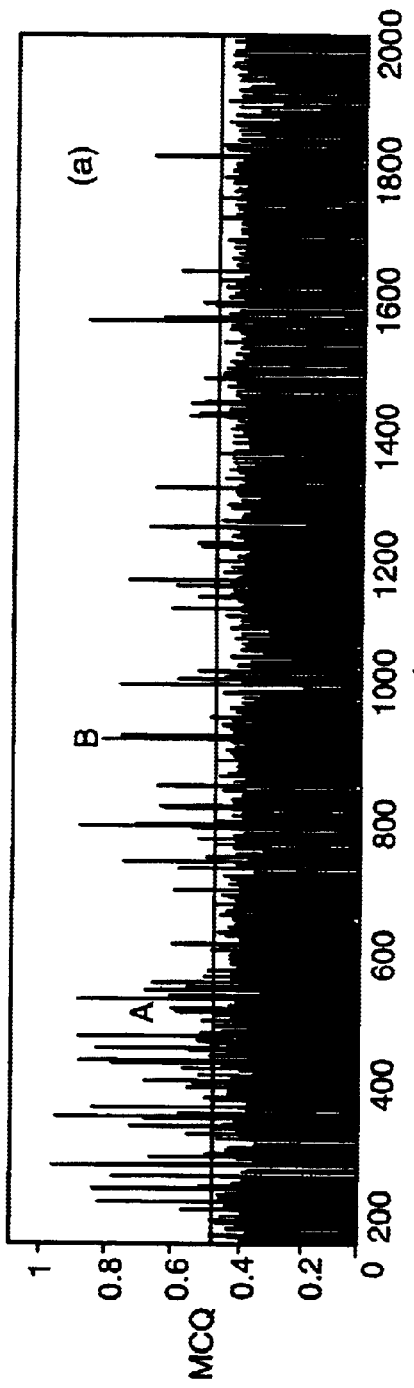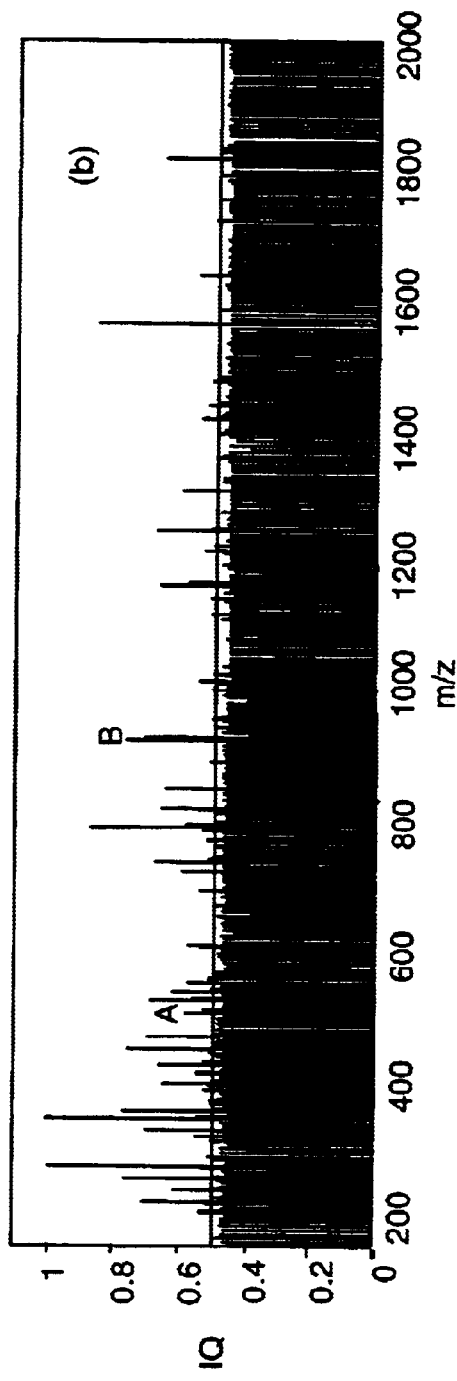
FIG. 6A
FIG. 6B

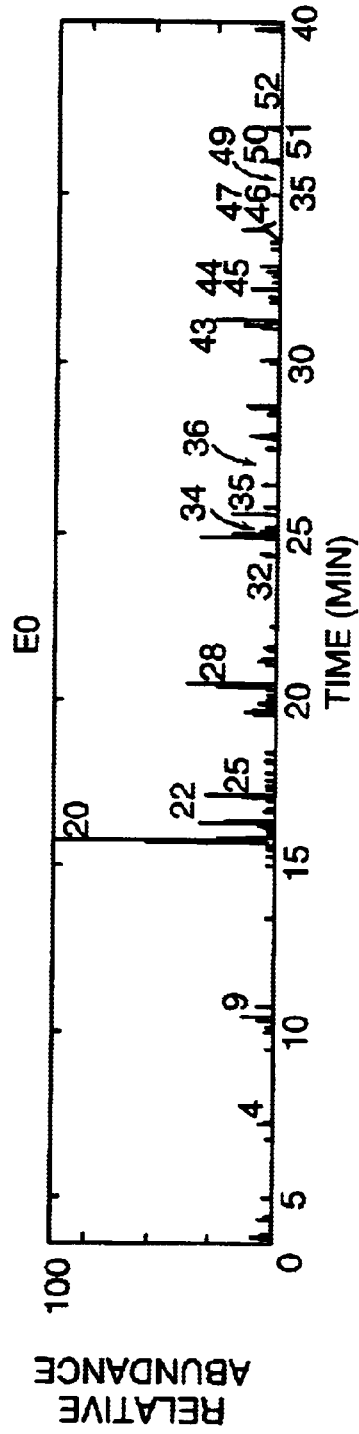
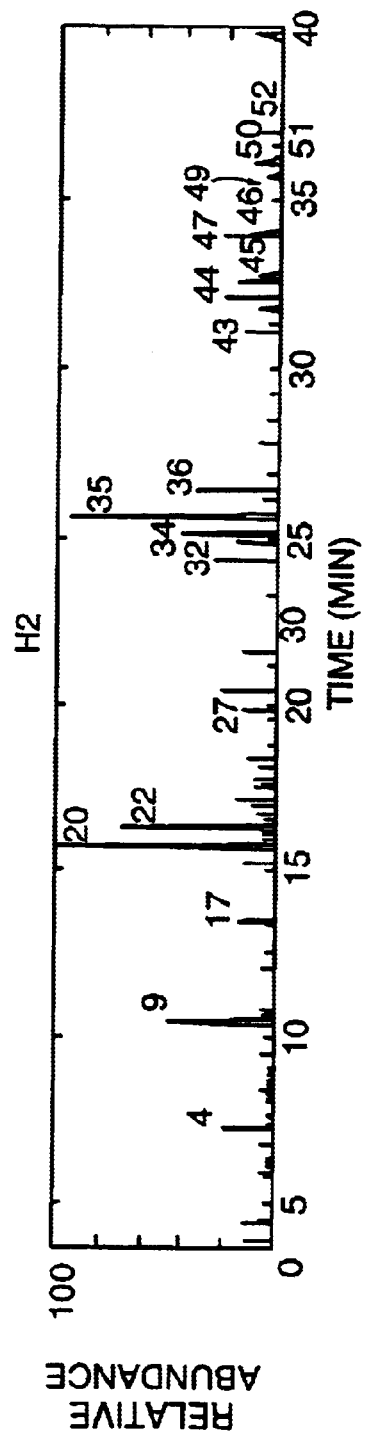

METHOD AND SYSTEM FOR IDENTIFYING AND QUANTIFYING CHEMICAL COMPONENTS OF A MIXTURE

CROSS REFERENCE TO RELATED APPLICATIONS

The present application claims the benefit of copending Netherlands patent application number 1015875 filed Aug. 3, 2000, and copending Netherlands patent application number 1016034 filed Aug. 28, 2000.

FIELD OF THE INVENTION

The invention relates to the field of data processing and evaluation. In particular, the invention relates to the processing and evaluation of mass chromatographic and mass spectrometric data.

BACKGROUND

Developments both in mass spectrometric technology and in the combination of mass spectrometers ("MS") with a broad variety of separation and micro-scale separation techniques, are quickly increasing the capacity of MS in terms of data production. Using modern instrumentation, the time required to obtain the above-mentioned data, such as chromatograms and mass spectra, is no longer the critical factor; rather, it is the time necessary for analyzing the data. In particular, a data set often comprises thousands of mass spectra measured over a mass-to-charge ("m/z") range of two to three orders of magnitude. An extended study using such a data set can occupy days if a complete analysis is required. In a research environment in particular, this analysis typically must be carried out by highly qualified, and consequently expensive, personnel.

In this context, the use of efficient data processing and evaluation to improve speed in data handling is highly desirable. Depending on the application, information extraction can be approached from different points of view. In impurity studies by capillary electrophoresis/mass spectrometry (CE/MS) or liquid chromatography/mass spectrometry (LC/MS), for example, data processing and evaluation tools must be able to perform efficient peak detection of compounds present at very low levels. On the other hand, if screening and comparison of very similar complex mixtures is to be performed, such as in the rapidly expanding field of proteomics, data processing and evaluation tools must be able to correlate data on multiple complex mixtures.

One prior approach to processing data produced by a combination of mass spectrometry and chromatography is U.S. Pat. No. 5,672,869 to Windig et al. ("the '869 patent"). The '869 patent describes a data processing approach which separates spurious peaks and noise by smoothing the raw data. This approach then compares processed and raw data. If a mass trace contains only background noise, the difference between raw and processed data is emphasized, and the algorithm assigns a low mass chromatographic quality ("MCQ") value to that particular mass trace. On the other hand, mass traces containing a peak are assigned high MCQ values. The '869 patent then teaches selecting only mass traces that possess a MCQ above an appropriate threshold value.

However, it is not necessarily clear what is an appropriate threshold value, especially for complex and/or noisy data. For example, by selecting a threshold which is too high, some relevant information on low intensity signals may be lost, while setting too low a threshold may select many "signals" that are actually just background noise. As a result, extensive visual examination of raw and processed data by trained personnel may be required to address this problem, and thereby lower data processing efficiency and speed.

A need therefore exists for a data processing technique that provides more efficient and clear data processing.

SUMMARY OF THE INVENTION

The present invention adapts an information content theory and combines it with data smoothing to provide a measure of data quality that better facilitates the efficient and clear evaluation of data. In particular, the present invention provides a measure of data quality based on what is referred to herein as an entropy value. The entropy value approach of the present invention improves data processing by providing less ambiguous thresholds for data selection. As a result, for example, the present invention speeds data processing by decreasing the amount of time trained personnel may be required to personally inspect and select data.

The present invention provides a method of data processing in which the separation between spurious peaks and noise on the one hand, and relevant data on the other hand, takes place more accurately and clearly, thereby shortening the data analysis time. Consequently, trained personnel can use their time interpreting the data. At the same time, the present invention provides the option of generating fingerprints of complex mixtures, which are increasingly being used in various fields (chemistry, pharmacy, medicine, biology, biotechnology, and the like), but particularly in the life sciences, for example, from the analysis of biological materials oriented towards DNA fragments, proteins and metabolic components.

In one aspect, the present invention provides a method of data processing and evaluation comprising the steps of smoothing the data points of a chromatogram and determining an entropy value for the smoothed-chromatogram. In one embodiment, the method also comprises the step of correcting the data points of a chromatogram for baseline prior to determination of an entropy value for the smoothed-corrected chromatogram. The chromatogram may be either a mass chromatogram or a total ion current ("TIC") chromatogram. It should be realized that the order of the smoothing and baseline correcting steps is unimportant to the present invention. That is, a chromatogram may be smoothed then baseline corrected, or baseline corrected and then smoothed. Accordingly, it is to be understood that the term "smoothed-corrected chromatogram" does not imply a specific order of practice.

In another embodiment, the method of the invention further determines a quality factor (i.e., an "IQ value") for a chromatogram based on the evaluation of entropy values for a plurality of chromatograms of a data set. In a preferred embodiment, the method selects individual chromatograms (of either corrected-chromatograms and/or smooth-corrected chromatograms) based on their IQ values. The method then uses these selected chromatograms to generate a reconstructed total ion current ("RIC") chromatogram. The method may further exclude from the RIC chromatogram one or more mass signals. In one embodiment, the one or more mass signals are selected for exclusion based on a mass signal quality value for the individual mass signals. In another embodiment, the method uses these selected chromatograms to generate a reconstructed mass chromatogram for one or more mass values. Further, in various embodiments, the RIC chromatograms are used as a fingerprint for comparison to other chromatograms of the same or other data sets.

In another aspect, the present invention provides a method of data processing and evaluation that correlates either a smoothed-chromatogram or a smoothed-corrected chromatogram with a plurality of chromatograms of a data set. The chromatogram of the smoothed-corrected-chromatogram (or smoothed-chromatogram) and the data set chromatograms may be, for example, a mass chromatogram, total ion current chromatogram, or a RIC chromatogram. In a preferred embodiment, the step of determining a correlation comprises using a multivariate analysis. Suitable forms of multivariate analysis include, but are not limited to, principal component analysis ("PCA"), discriminant analysis ("DA"), partial least squares ("PLS"), predictive linear discriminant analysis ("PLDA"), neural networks, and pattern recognition techniques.

In another embodiment of the present invention, the entropy values of a plurality of smoothed mass chromatograms are each calculated and stored, followed, if desired, by processing of these entropy values or, as the case may be, components selected according to these entropy values by means of chemometric and biometric methods. Preferred forms of component selection include multivariate analysis techniques (PCA, DA, PLS, PLDA, neural networks), pattern recognition techniques and Fourier transform techniques. In another embodiment, the selected components are further used to generate a fingerprint and that is used, in conjunction with chemometric and biometric techniques, as a characterization method for complex mixtures of various origins.

In another aspect, the present invention provides a system for data processing and evaluation. The system is characterized in that it comprises a smoothing device for smoothing the data points of a mass chromatogram and an entropy calculation device for determining the entropy value of a mass chromatogram. In one embodiment, the system further comprises a baseline correction device for correcting the baseline of a chromatogram. Preferably, the system comprises a chromatograph for separating the components of the mixture and a spectrometer to which the separated components are delivered. In one embodiment, the system further comprises a storage device for storing the entropy values.

In another aspect, the method and system of the present invention relates to methods for identifying and quantifying chemical components of a mixture of materials the method generally comprises the steps of: (1) subjecting the mixture to a separation method to separate the components of the mixture into separate materials; (2) subjecting the separated materials to mass spectrometry to detect and to identify the components, and to obtain a total ion current ("TIC") chromatogram (or ion electropherogram) and mass spectra; (3) selecting masses from the mass spectra; and (4) obtaining mass chromatograms for each mass.

The foregoing and other features and advantages of the invention, as well as the invention itself, will be more fully understood from the description, drawings, and claims which follow.

BRIEF DESCRIPTION OF THE DRAWINGS

FIGS. 6A and 6B show a comparison of MCQ and IQ plots for an LC/MS run of digested BSA 500 nM according to Example 1.

FIGS. 9A–9D show gas chromatography/mass spectrometry (GC/MS) TIC chromatograms for the set of experiments identified as H in Examples 1 and 2.

DETAILED DESCRIPTION

Figure 1:
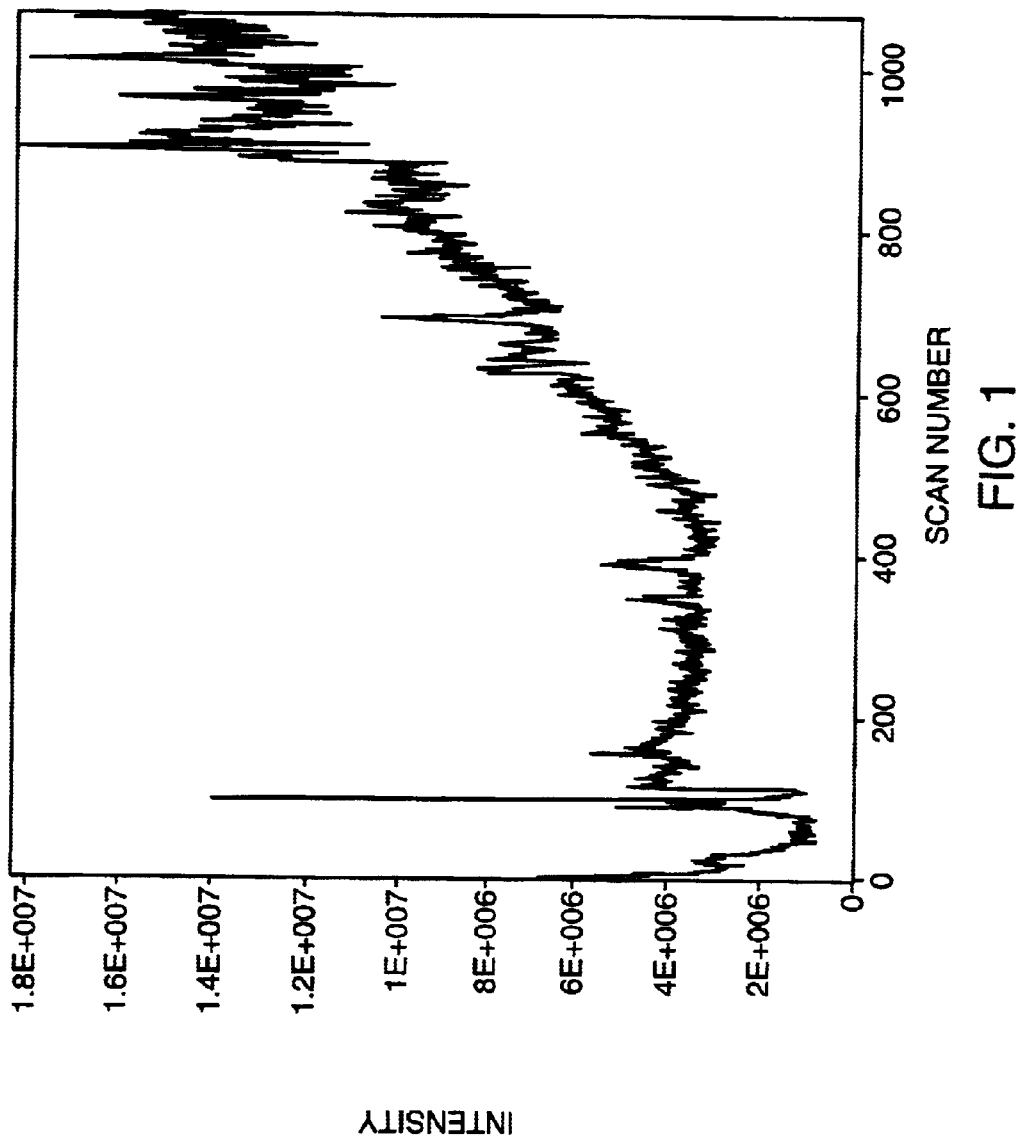
FIG. 1 shows an example of a total ion current (TIC) chromatogram as obtained by means of a liquid chromatograph in combination with a mass spectrometer (LC/MS).

The detection, identification and quantification of components in a mixture (or material) frequently makes use of the combination of chromatography (or electromigration) and spectrometry. FIG. 1 shows an example of a total ion current ("TIC") chromatogram obtained by a combination of liquid chromatography and mass spectrometry ("LC/MS").

Chromatography is primarily used as a separation technique. The molecules of the mixture to be separated are exchanged many times between a mobile phase and a stationary phase. The rate at which this happens depends on many factors, for example, on the mobility of the separate molecules, the temperature, and the binding forces. The difference in the time which each species of molecule remains in the mobile phase results in a difference in transport rate and in the separation of substances. Despite the differences in transport rates for various species, the specificity of conventional chromatography is generally insufficient to allow for identification of the separated components. Therefore, a chromtography technique typically is used in series with another analysis technique. A technique commonly used in combination with chromatography is mass spectrometry.

In a conventional LC/MS technique, the chromatography device (or chromatograph) is linked to a mass spectrometer that repeatedly scans the mobile phase as it emerges from the chromatograph. Each scan of the mass spectrometer produces a mass spectra. Thus, a large number of mass spectra often are recorded for each analysis, producing a very extensive data set. Typically, a plurality of spectra are obtained which contain only "background" since when the mass spectrometer begins scanning typically no components of interest emerge from the chromatograph. When mobile phase containing a component exits the chromatograph, the mass spectra generally exhibit a change that depends, for example, on the type of component entering the mass spectrometer. Typically, each mass spectrum (or scan) contains a number of ions, which together produce a total ion current associated with that spectrum. FIG. 1 shows, for an LC/MS technique, a example plot of this total ion current (e.g., intensity) for each mass spectra (i.e., scan) as a function of time (e.g., scan number). FIG. 1 thus illustrates a total ion current ("TIC") chromatogram. This total ion current chromatogram is generally the raw data of the LC/MS technique and forms the basis for component detection. An alternative graph is that of an individual mass-to-charge ratio as a function of time (e.g., scan number), this graph being generally known as a mass chromatogram.

The methods of the present invention may use data obtained from a combination of a chromatography method and mass spectrometry method. Suitable chromatography (i.e., separation) methods include, among others, gas chromatography ("GC"), liquid chromatography ("LC"), electromigration methods, electrophoresis, capillary electrochromatography ("CE"), isoelectric focusing, and supercritical liquid chromatography. Suitable types of mass spectrometry, include, but are not limited to, ion traps, time-of-flight MS, Fourier transform MS, quadrupoles, sector instrumentation or multiple combinations of MS hardware designs. Multiple combinations of MS hardware include, among others, triple quadrupoles (QQQ), QTOF, ion trap/sector instruments, quadrupole sectors, and high-resolution mass chromatography. Other combinations of chromatography and mass spectrometry may be used, including, but not limited to, LC/NMR, LC/UV, LC/MS/MS, GC/MS, CE/MS, CEC/MS, ITP/MS, IEF/MS, SFC/MS.

The data smoothing according to the invention may be performed by any of a number of procedures known to the art. Preferably, smoothing is performed using a Savitsky-Golay function. In one embodiment, the Savitsky-Golay function with a selectable smoothing window W and a selectable smoothing order O is used. In one embodiment, and values of W=8 and O=2 are used. In one embodiment, the method of the present invention then determines an entropy value for the smoothed-chromatogram. In another embodiment, the entropy value determination is preceded by correcting the mass chromatogram for baseline to produce a smoothed-corrected chromatogram.

The baseline correction according to the invention is based on the assumption that the baseline runs though all peaks of a chromatogram even where no peaks are present. In one embodiment, the first and second derivatives of the chromatogram first are evoked to decide where peaks are present. A baseline function is then plotted through the remaining data points of the chromatogram. In one embodiment, the baseline function comprises a spline function, such as a cubic spline interpolation. This baseline function is used to correct each data point of the original chromatogram by the predicated height of the baseline at that point. This produces a corrected-chromatogram. In a preferred embodiment, the function is plotted with the aid of the Savitsky-Golay algorithm.

The Savitsky-Golay algorithm and "smoothing" are described in Numerical Recipes in C, second edition, The Art of Scientific Computing, W. H. Press, B. P. Flannery, S. A. Teukolsky, W. T. Vetterrling, Cambridge University Press, 1988, ISBN 0-521-35465-X.

In one embodiment, the first and second derivatives of the chromatogram first are evoked to decide where peaks are present, and mass chromatograms containing chemical information (e.g., peaks) are selected for inclusion in the TIC chromatogram, whereas mass chromatograms containing substantially only background noise or spurious peaks are excluded from the TIC chromatogram. Thus, the signal-to-noise ratio in the resultant TIC chromatogram is considerably increased by the selective exclusion of chromatograms containing substantially only noise.

In another embodiment, only mass spectra that fall within a certain time window (e.g., scan number range) are selected for processing. For example, it may not be desired to process mass spectra from low scan numbers (i.e., earlier times) because, for example, such spectra may contain only mobile phase and no chemical or biological information of interest (e.g., a component). Similarly, mass spectra from high scan numbers (i.e., late times) may not contain any discernable chemical or biological information. That is, all the components of interest already may have exited the chromatograph.

After baseline correction and/or data point smoothing, methods of the present invention determine an entropy value for the smoothed (or smoothed and corrected) chromatogram substantially according to the formula, $$H = \sum_i p_i \ln(p_i) \qquad \text{Eq. (1),}$$

where H is the entropy value, and $p_i$ is the intensity value of the $i^{th}$ data point of the chromatogram. Equation 1 is also described in Numerical Recipes in C in connection with game theory. In another embodiment, the entropy value is determined substantially according to the formula, $$H = \sum_i p_i^2 \ln(p_i^2) \qquad \text{Eq. (2),}$$

where H and $p_i$ have the same meaning as above. In other embodiments, the entropy value H of equations 1 and/or 2, is the negative of the sum of the right-hand side of these equations. However, it is not central to the present invention whether the entropy is expressed as a positive or negative value.

In one embodiment, a TIC chromatogram is generated from mass chromatograms which are weighted by a weight based on the entropy value associated with each individual mass chromatogram (i.e., entropy-weighted). The resultant TIC chromatogram is one version of a RIC chromatogram according to the present invention.

In another embodiment, mass chromatograms (which have been corrected or smoothed and corrected) are selected for inclusion in the TIC chromatogram based on the entropy value of the individual chromatogram. In one embodiment, the selection is based on a quality factor ("IQ") that is the reciprocal of the entropy value. In another embodiment, the IQ is the negative reciprocal of the entropy. However, as previously explained, a simple change in sign of an IQ value (or entropy value) has substantially no substantive effect on the practice of the present invention. Preferably, IQ values are scaled between zero and one by dividing individual IQ values by the maximum IQ value determined for a data set.

In a preferred embodiment, selection of chromatograms and determinations based on entropy values are based on a quality factor ("IQ") that is determined substantially according to the formula, $$IQ = 1 - (H/H_{max}) \qquad \text{Eq. (3),}$$

where IQ is the quality factor, H is the entropy value of the smoothed-corrected-chromatogram (or smoothed-chromatogram), and $H_{max}$ is the maximum entropy value determined for the chromatograms of the data set. As above, in other embodiments, the IQ values of equation 3, is the negative of the right-hand side of this equation. Accordingly, chromatograms with a high absolute IQ value (low entropy) typically contain an intense signal and little noise. Chromatograms with a low absolute IQ value typically contain much noise and little signal. Ordering chromatograms (either mass, TIC or RIC chromatograms) with respect to their IQ value permits differentiation of chromatograms according to their information content, thereby allowing useful signal traces to be separated from substantially noise traces.

Figure 2:
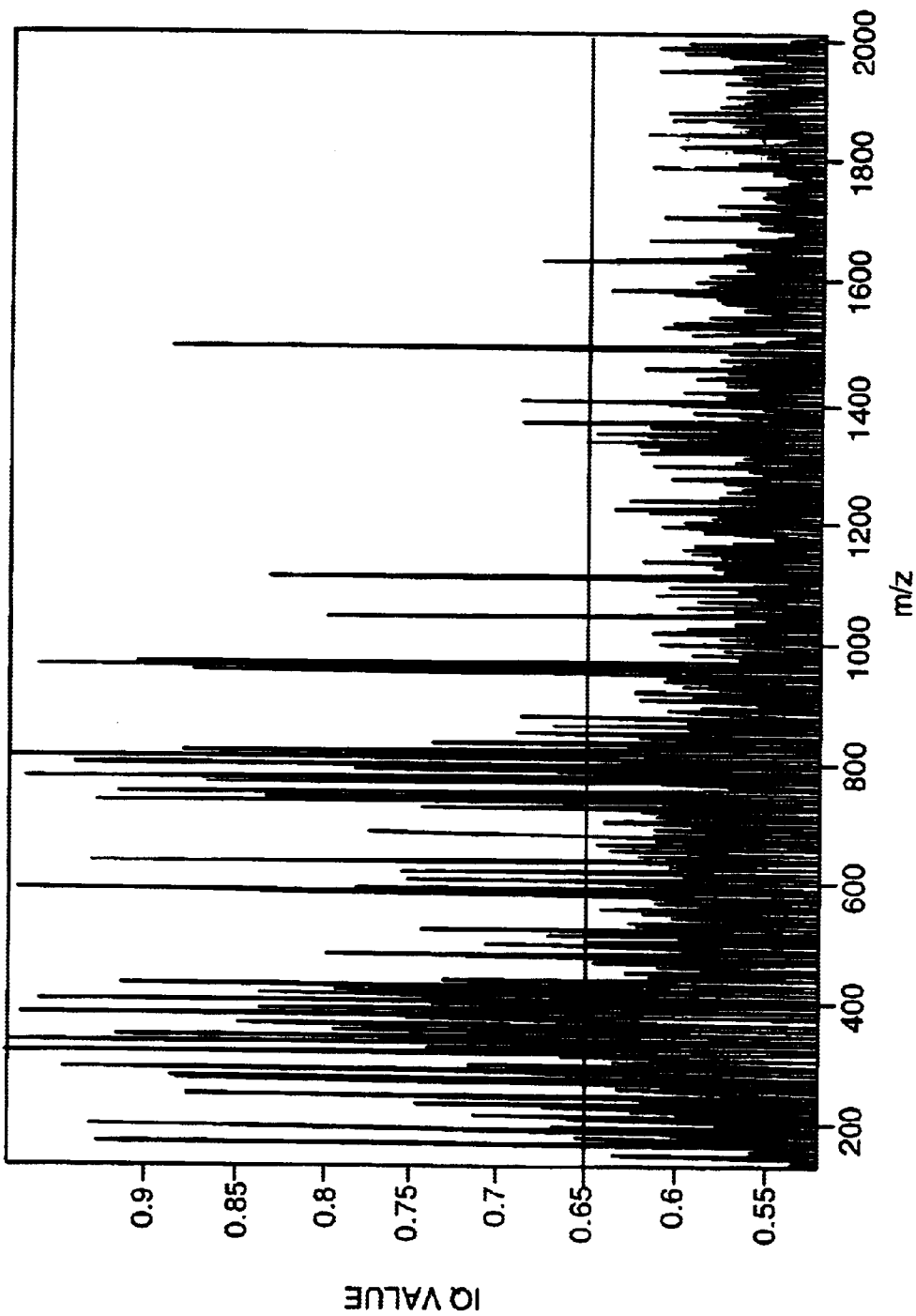
FIG. 2 shows an example plot of calculated IQ values of chromatograms, i.e., and IQ spectrum.

FIG. 1 shows a TIC chromatogram for a mixture obtained by LC/MS. The TIC chromatogram of FIG. 1 is raw data, i.e., data which has not been processed according to the present invention. FIG. 2 shows the entropy values of the mass chromatograms that comprise FIG. 1, where the entropy values are presented as quality factors IQ. Accordingly, the x-axis of FIG. 2 is the mass-to-charge ratio ("m/z") associated with the mass chromatogram and the y-axis is the IQ value of the mass chromatogram. Also plotted as a horizontal line is a selected IQ threshold value. In sum, FIG. 2 illustrates selection of mass chromatograms on the basis of an entropy value.

In one embodiment, the mass chromatograms thus selected are used to generate a reconstructed total ion current ("RIC") chromatogram. In one embodiment, the selected chromatograms are entropy-weighted. In another embodiment, the ion current associated with a selected mass chromatogram is set equal to that of the most intense value in the mass chromatogram. This latter RIC chromatogram generation approach is referred to herein as an IQ intensity-weighted RIC chromatogram.

Figure 3:
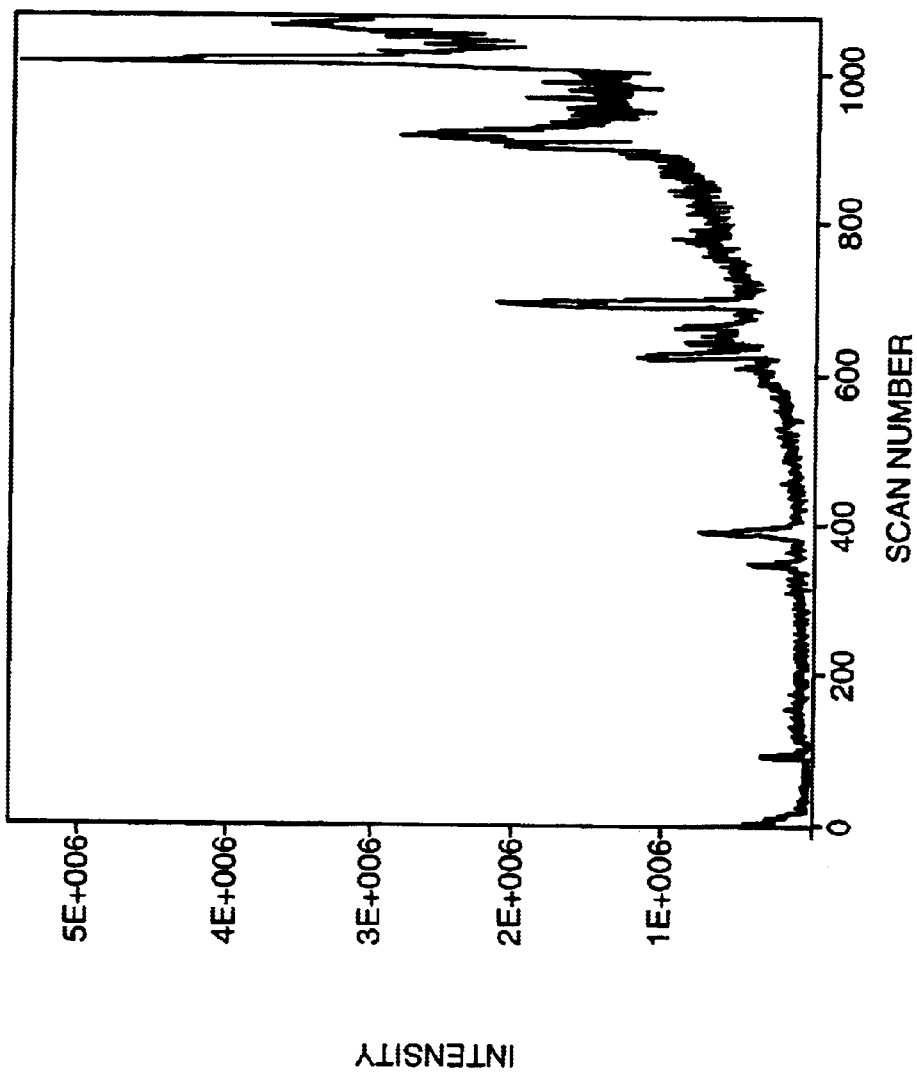
FIG. 3 shows a reconstructed total ion current (RIC) chromatogram for the TIC chromatogram of FIG. 1.

FIG. 3 depicts a RIC chromatogram for the TIC chromatogram of FIG. 1. The RIC chromatogram of FIG. 3 was generated according to the methods of the present invention by selecting mass chromatograms with an IQ value above the threshold value shown in FIG. 2. Comparison of the chromatograms of FIGS. 1 and 3 clearly shows a considerable reduction in noise. The peaks now are readily discernible over the noise.

In one embodiment, the present invention further excludes one or more mass signals from the RIC chromatogram. In one embodiment, masses associated with a particular component are excluded. Such components may include, for example, the mobile phase, the stationary phase, and/or known or suspected contaminants. Such contaminants may comprise, for example, part of the mixture under analysis or those associated with the chromatographic or mass spectrometric technique. In another embodiment, the one or more mass signals are selected for exclusion based on a mass signal quality value for the individual mass signals. The mass signal quality factor may be based on an entropy value for an associated mass spectrum or mass chromatogram, such as provided by Eqs. (1) to (3), or may be based on some other measure of mass signal quality, such as signal-to-noise ratio.

In another embodiment of the invention, a RIC chromatogram is generated excluding a selected group of one or mass signals therefrom, however, this exclusionary operation is continued until no peaks remain in the RIC chromatogram.

In another embodiment, instead of using the intensity sum per time unit as a chromatogram (e.g., a TIC chromatogram), the present invention employs an entropy value summed per unit time, resulting in a total entropy chromatogram ("TEC"). Moreover, in one version of this embodiment where chromatograms are selected based on entropy values, the resultant chromatogram comprises a reconstructed entropy chromatogram ("REC").

In addition, in one embodiment, mass chromatograms are sorted according to the probability that they contain relevant peaks or according to the probability that they are associated with a particular component. As will be illustrated below, the data processing based on entropy values provides a less ambiguous threshold value for chromatogram selection. For example, the RIC chromatograms generated according to the present invention provide a very good aid to the operator in the analysis of a mixture.

Figure 4A:
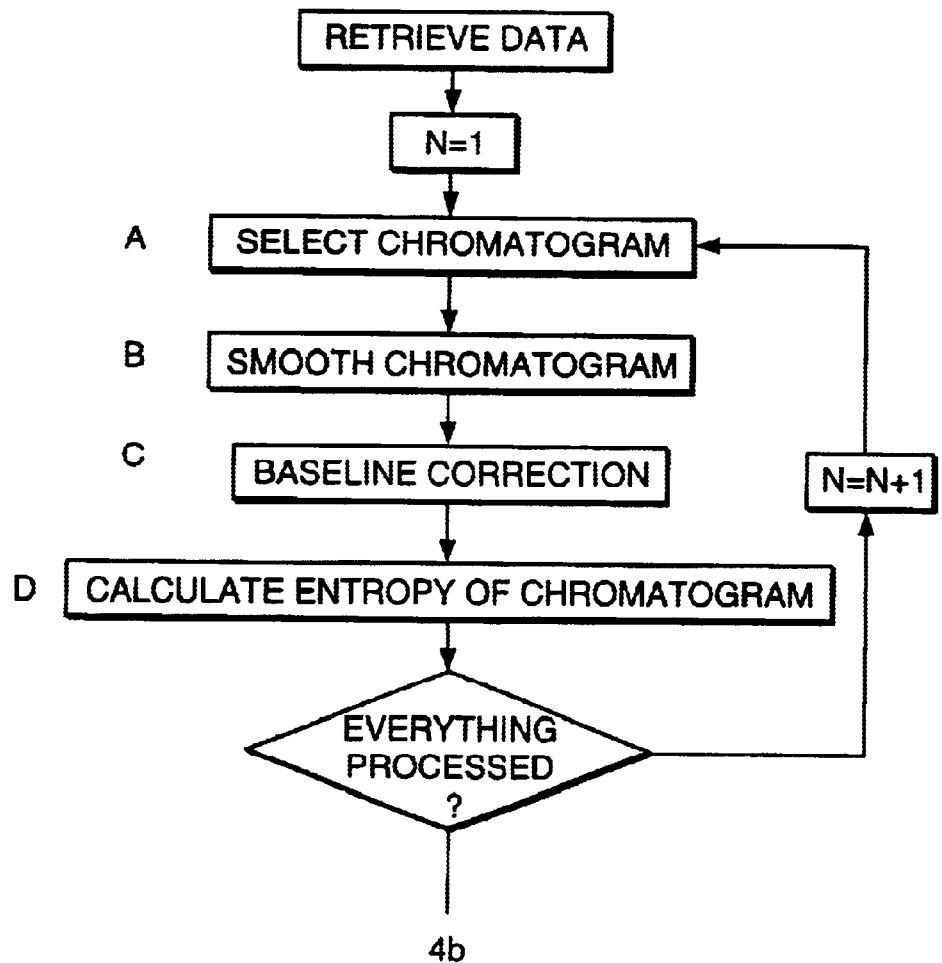
FIGS. 4a and 4b are flow diagrams of embodiments of methods of the present invention.
Figure 4B:
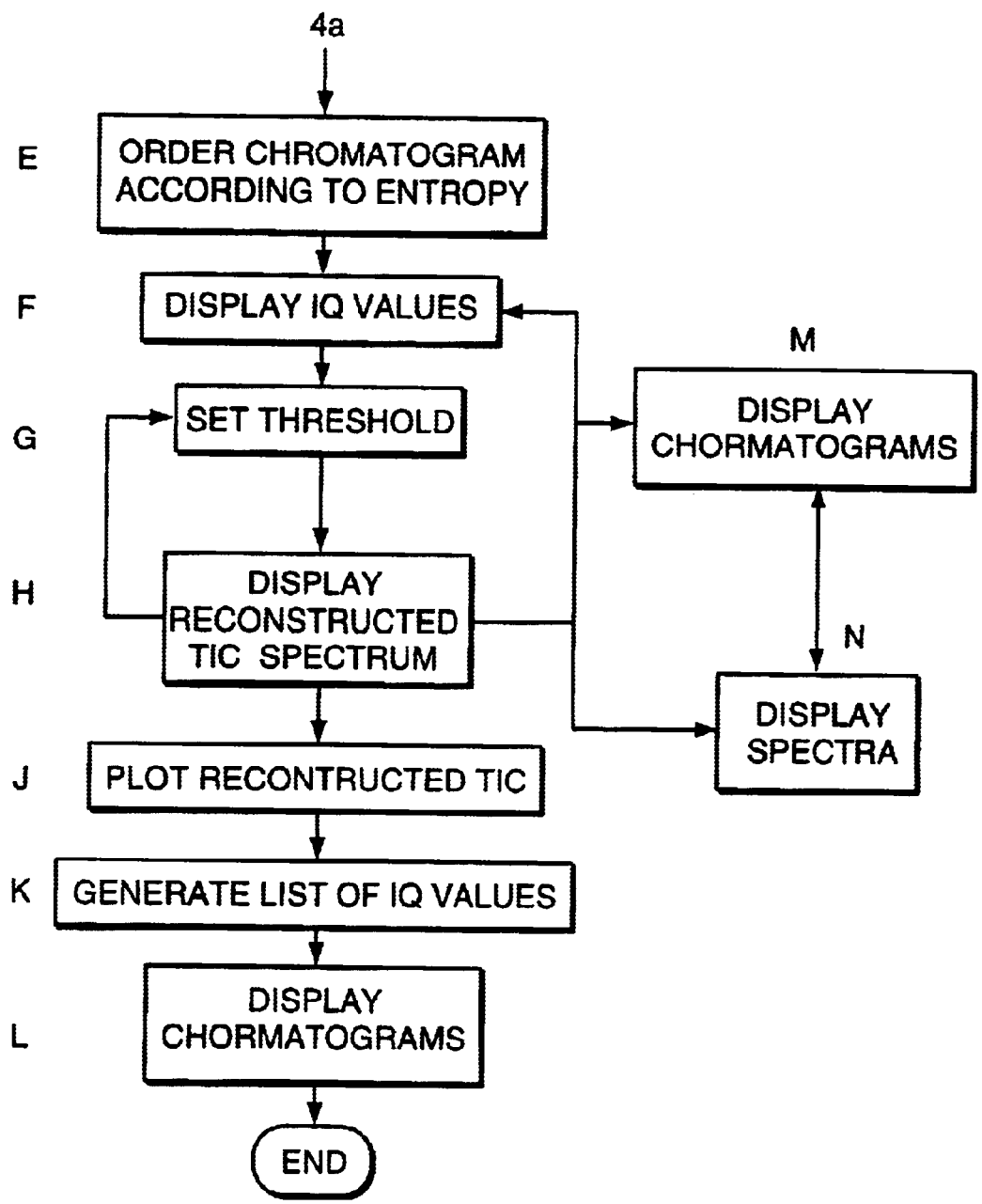

Referring to FIGS. 4a and 4b, various embodiments of methods of the invention for processing data obtained from a chromatographic-mass spectrometry instrument (e.g., LC/MS) are shown. In one embodiment, a method of the present invention begins by selecting a chromatogram (box A). The selected chromatogram is smoothed (box B), and then a baseline correction is performed (box C). The sequential order of smoothing and baseline correction can also be reversed. After the smoothing step and the baseline correction step have been performed, the entropy of the smoothed-corrected-chromatogram is determined (box D). As illustrated by the loop via (N=N+1), these steps of boxes A, B, C and D may be performed for a plurality of chromatograms until all desired chromatograms are processed (i.e., "YES" to the question "Everything processed?").

Referring to FIG. 4B, the mass chromatograms may be ordered in accordance with entropy value and/or a quality factor IQ (box E), and displayed if desired (box F). In one embodiment, based on the displayed IQ values (e.g., as in FIG. 2), a threshold value may be set (box G). In one embodiment of the method, a RIC chromatogram is generated from the smoothed-corrected-chromatograms that have an IQ value above the threshold value.

Those selected mass chromatograms whose entropy value exceeds the set entropy threshold value (as indicated by the loop line between box H and G). are then used to generate a reconstructed TIC (i.e., a RIC) chromatogram, box J. In one embodiment, the method also (box K), generates a list of relevant entropy values and displays the selected smoothed-corrected chromatograms, box L. Further, as indicated by boxes M and N, in one embodiment, the chromatograms and/or the selected mass spectra may be displayed if desired in any of the steps of boxes F, G and H, to facilitate the analysis of the data.

In another aspect, the present invention provides a method of data processing and evaluation that correlates chromatograms (processed or generated by the methods of the present invention) with a plurality of chromatograms of a data set. In one embodiment, the present invention correlates a RIC chromatogram with one or more TIC chromatograms or RIC chromatograms of the same or different data sets. Accordingly, in various embodiments, the RIC chromatogram may serve as a fingerprint for a mixture which may be later compared to other known or unknown mixtures by means of chemometric/biometric techniques. In another embodiment, an entropy-weighted RIC chromatogram is used as a fingerprint. In another embodiment, an IQ spectrum is used as a fingerprint.

Figure 5:
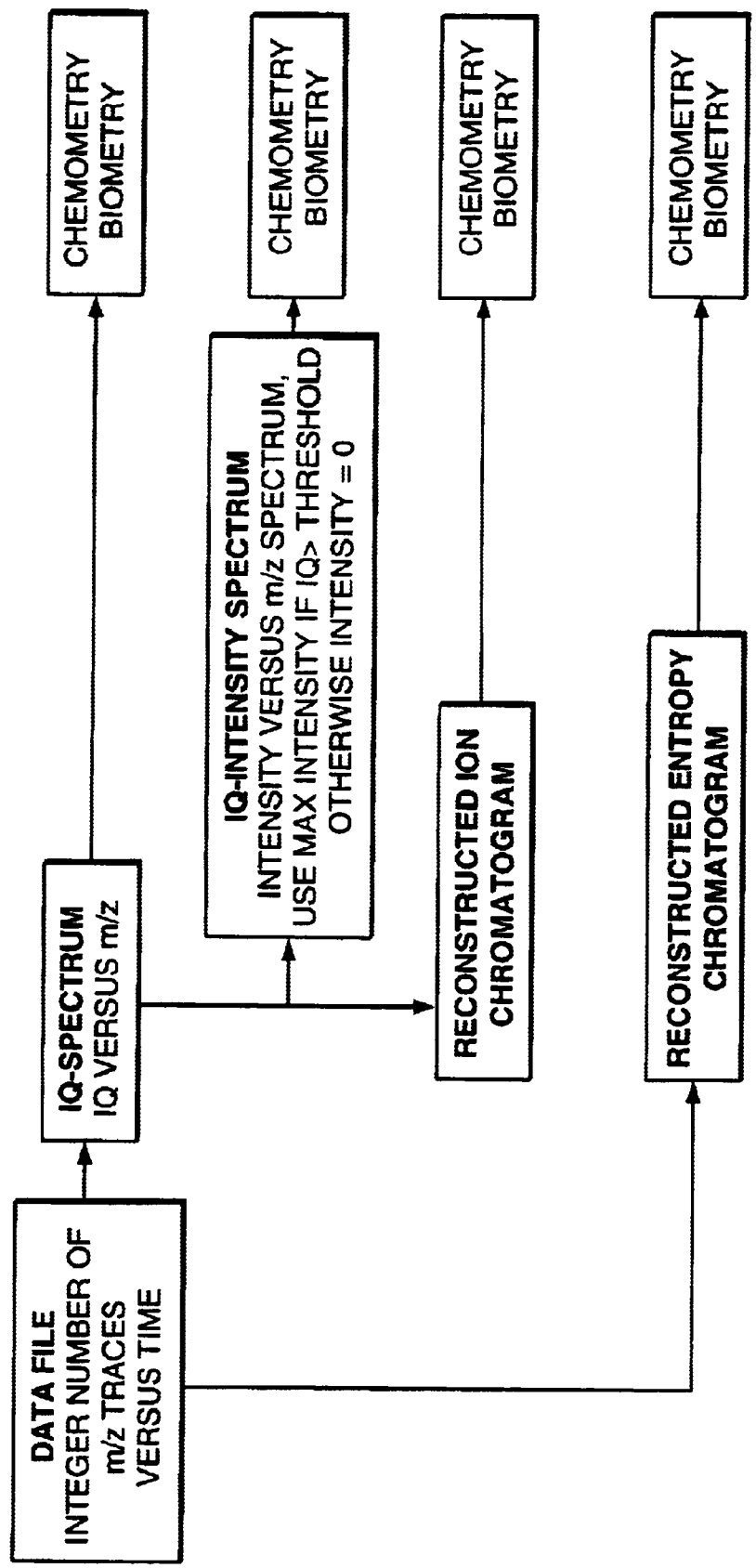
FIG. 5 is a flow diagram of embodiments of processing the selected or entropy-weighted components by means of biometric/chemometric techniques.

The present invention provides various embodiments of generating a fingerprint of a mixture as illustrated in FIG. 5. Each embodiment of FIG. 5 starts with a data set comprised of mass chromatograms (i.e., m/z traces versus time). In one embodiment, IQ values as a function of the m/z value are determined to generate an IQ spectrum (an example of which is shown in FIG. 2) and the IQ spectrum is then used as an input for a multivariate data processing operation. In one embodiment, the total IQ spectrum is used, and in other embodiments, an IQ threshold is employed. In still another embodiment, the IQ intensity-weighted RIC chromatogram is used as an input for a multivariate data processing operation.

In another embodiment illustrated in FIG. 5, a RIC chromatogram is used as an input for a multivariate data processing operation. In another embodiment, instead of using the intensity sum per time unit as an input chromatogram, an entropy value summed per unit time, i.e., a REC chromatogram is used as input for a multivariate data processing operation. In another embodiment, e.g., in the case where no selection is made of the mass chromatograms based on entropy values, the TIC chromatogram is used as an input for a multivariate data processing operation. Equally, in the case of no selection, one embodiment employs a TEC chromatogram as an input. The combination of evaluations by a multivariate analysis of both the m/z dimension and the time dimension in one or more forms, with and without entropy selection, provides a novel way of characterizing complex mixtures by means of separation methods linked to spectrometry.

In certain embodiments, smoothed-mass chromatograms (or smoothed-corrected-mass chromatograms) are used as fingerprints for identification of a chemical component. In one embodiment, the correlation between the smoothed-mass chromatogram (or smoothed-corrected-mass chromatogram) associated with a selected mass and all the other mass chromatograms is determined. The mass chromatograms then may be evaluated based on their correlation coefficient.

In some embodiments, the functionality of the methods described above may be implemented as software on a general purpose computer. In addition, such a program may set aside portions of a computer's random access memory to provide a baseline correction device, smoothing device, an entropy value device for determining entropy values, a selection device for selecting chromatograms based on their entropy values, and the operations with and on the chromatograms and mass spectra. In such an embodiment, the program may be written in any one of a number of high-level languages, such as FORTRAN, PASCAL, C, C++, or BASIC. Further, the program may be written in a script, macro, or functionality embedded in commercially available software, such as EXCEL or VISUAL BASIC. Additionally, the software could be implemented in an assembly language directed to a microprocessor resident on a computer. For example, the software could be implemented in Intel 80×86 assembly language if it were configured to run on an IBM PC or PC clone. The software may be embedded on an article of manufacture including, but not limited to, a "computer-readable medium" such as a floppy disk, a hard disk, an optical disk, a magnetic tape, a PROM, an EPROM, or CD-ROM.

Experimental Approach of the Examples

The examples share the experimental approach described below. The examples describe evaluation of data obtained by CE/MS, LC/MS, and/or GC/MS techniques.

Reagents and Materials

Acetonitrile was purchased from Biosolve B. V. (Valkenswaard, The Netherlands), whereas methanol, formic acid and acetic acid were from Merck (Darmstadt, Germany). Water was purified through an ELGA system. Ammonium acetate, trypsin, bovine serum albumin (BSA), dithiothreitol (DTT) and cytochrome C were purchased from Sigma (Deisenhofen, Germany). Iodoacetamide was from Fluka (Buchs, Switzerland). Hexametrine dibromide (polybrene) was from Aldrich (Steinheim, Germany).

CE/MS Technique

The CE/MS measurements were conducted on an LCQ (Thermoquest, San Jose, Calif., USA) mounted with a nanoelectrospray x-y-z positioner from Protana (Odense, Denmark) instead of the conventional ESI interface. The CE instrument was a Prince from Prince Technologies (Emmen, The Netherlands). The CE capillaries used, 20 $\mu$m inner diameter (i.d.), 65 cm long, tapered and gold coated, were from New Objective (Cambridge, Mass., USA); they were connected to the nozzle of the x-y-z positioner via conductive paste Leit C (Protana). The inner walls of the CE capillary were coated with a 5% w/v polybrene solution in 2% ethylene glycol v/v at the beginning of the day using a modification of the method described by Bateman et al. in *Rapid Comm. Mass Spectrom.,* vol. 11, p. 307 (1997). The sequence of coating steps was performed at 2 bar pressure and was as follows: polybrene solution (20 minutes), water (5 minutes), background electrolyte (20 minutes). The background electrolyte ("BGE") was 50 mM AcOH in 50% MeOH v/v. Separations were performed by applying −25 kV potential at the injection end of the capillary and +1.7 kV at the nanoelectrospray tip. Injection volume was about 3 nL.

LC/MS Technique

The LC/MS measurements were conducted on an LCQ DECA (Thermoquest, San Jose, Calif., USA) using a conventional ESI source in positive ion mode detection. The spray voltage was 3.5 kV, whereas the heated capillary temperature was 250° C. The eluent flow of 25 $\mu$L/min was provided by an Eldex micro LC (Separations). Analyses were conducted on a 15 cm×800 $\mu$m i.d. column packed with spherisorb $C_{18}$-silica, particle size 5 $\mu$m, purchased from LC Packings (Amsterdam, The Netherlands). The injection loop was 5 $\mu$L. Gradient elution was performed. Mobile phase A: 10 mM $NH_4OAc$ in 0.1% HCOOH v/v; mobile phase B: 10 mM $NH_4OAc$ in 0.1% HCOOH v/v 80% MeCN v/v. Gradient: 0 min-10% B/10 min-30% B/25 min-60% B/30 min-100% B.

GC/MS Technique

Mass spectrometric detection was performed by an HP 5973 MSD system via an electron impact source. Electron energy was 70 eV, source temperature 230° C. Gas chromatography was performed using an HP 6890 GC system, on a 30 m×320 $\mu$m i.d. column coated with DB5-MS. Helium flow was 48 cm/sec, and the temperature gradient was: 0 min-25° C./4 min-25° C./10 min-75° C./22 min-135° C./24 min-250 ° C./30 min-250° C. Prior to multivariate analysis, a shift routine was applied to the TIC chromatograms of the entire data set in order to correct for small retention time variations. Data analysis of the GC-MS TIC profiles was carried out by MATLAB (The MathWorks, Inc., Natick, Mass., USA).

Protein Digestion

Bovine serum albumin was reduced by DTT and carbamidomethylated using iodoacetamide before digestion by trypsin (enzyme/substrate ratio 1:30). Cytochrome C was digested without being first denatured. Digestion was carried out overnight at 37° C. in 100 mM $NH_4HCO_3$ buffer, pH 7.5. The final concentration of BSA digested samples used for PCA analysis was 10 $\mu$M.

Sausage Fermentation

GC/MS profiles of volatile compounds were acquired from sausage batters which were inoculated with bacterial strains (Lactobacillus FC 1, *Staphylococcus carnosus*) and their corresponding cell free enzymic extracts (Table 1). Sampling (Likens-Nickerson extraction) and subsequent analysis by GC-MS was done before inoculation and at three different time points (t=24, 66 hrs and 3 weeks) during fermentation. In addition, a control experiment without inoculation was conducted.

TABLE 1

Experimental set-up for sausage batters inoculation.

| Experiment | Bacterial strain ($10^7$ cells) | Cell free extract ($10^9$ cells) |
|---|---|---|
| B | Lactobacillus | — |
| C | — | Lactobacillus |
| D | Lactobacillus | Lactobacillus |
| E (control) | — | — |
| F | Lactobacillus + Staphylococcus | |
| G | Lactobacillus | Staphylococcus |

TABLE 1-continued

Experimental set-up for sausage batters inoculation.

| Experiment | Bacterial strain (10⁷ cells) | Cell free extract (10⁹ cells) |
|---|---|---|
| H | Lactobacillus + Staphylococcus | Staphylococcus |

EXAMPLE 1

Comparison to MCQ Approach

The first example compares the evaluation of LC/MS and CE/MS data by means of the CODA algorithm of Windig et al., *Anal. Chem.* Vol. 68, p. 3602 (1996), and the methods of the present invention. The comparison was performed on LC/MS and CE/MS data. Concerning CE/MS data, additional challenges were represented by the presence of spikes in the electropherogram and by the sharpness of the peaks.

The CODA algorithm assigns an MCQ value for all integer m/z value mass chromatograms of a raw datafile. A high MCQ value is an indication that a particular mass trace contains a peak. By selecting a threshold MCQ, and by rejecting the mass traces (i.e., mass chromatograms) having an MCQ value below the chosen threshold, only certain chromatograms are selected for genration of a RIC chromatogram.

The methods of the present invention were also used to process the data and assign an IQ value (determined substantially in accord with equation 3) for all integer m/z value mass chromatograms of a raw datafile. A high IQ value is a strong indication that a particular mass trace contains a peak. As described above, a threshold IQ value is used to select mass chromatograms to compile a TIC chromatogram and/or generate a RIC chromatogram.

For LC/MS data, the methods of the present inventions show improved performance over the CODA algorithm, as shown in FIGS. 6A and 6B, where MCQ and IQ plots are compared. The sample examined in this case was an LC/MS analysis of a BSA digest at 500 nM concentration. It can be easily seen from the comparison of FIG. 6A (the MCQ plot) to FIG. 6B (the IQ plot), that setting a precise cut-off value was much easier in the IQ plot (FIG. 6B). On the contrary, in the MCQ plot a compromise had to be chosen: by using a too high threshold, some potential relevant information in the low m/z region would have been lost (see FIG. 6A), while setting a too low threshold would have selected many high m/z values that were just background noise.

Figure 7B:
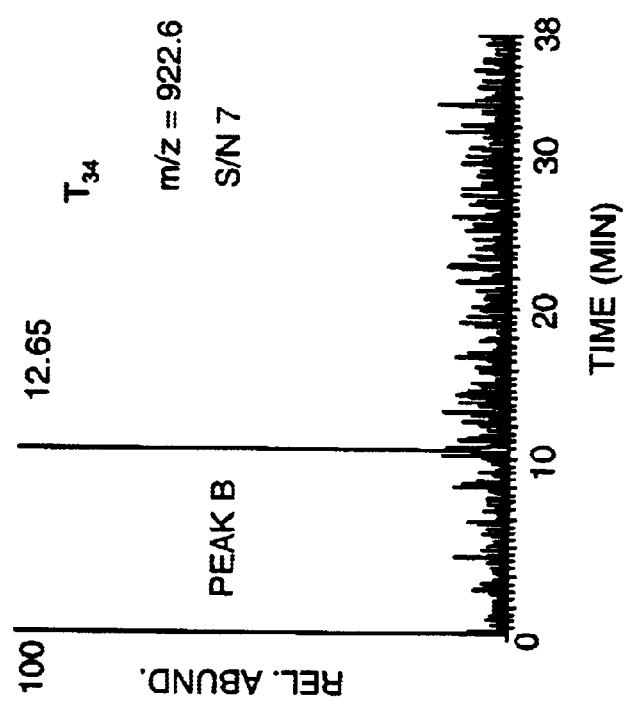
FIGS. 7A and 7B show the peaks marked as "A" and "B", respectively, in FIGS. 6A and 6B.
Figure 7A:
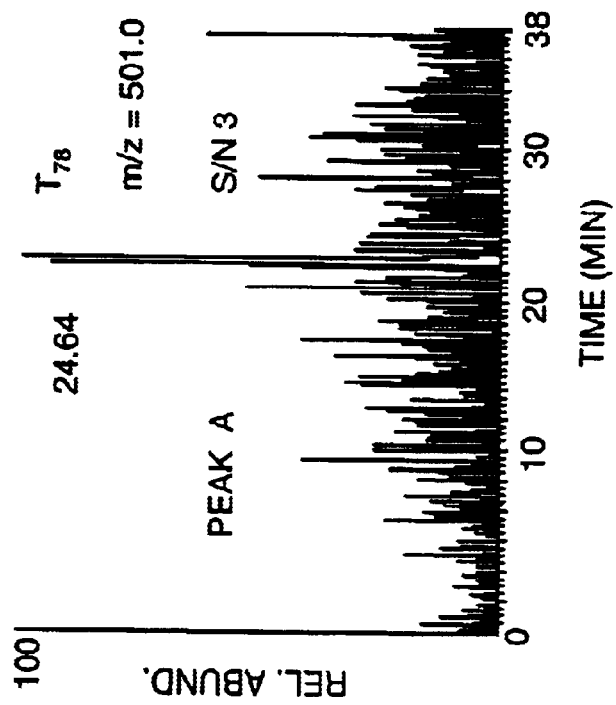

As evidence that the present invention could detect very low S/N peaks, two example peaks from FIGS. 6A and 6B are shown in FIGS. 7A and 7B. Peak A is shown in FIG. 7A, while Peak B is shown in FIG. 7B. The two tryptic digest fragments peaks A and B were detected by LC/MS with, respectively, a S/N ratio of 3 and 7, nevertheless, they were assigned with MCQ and IQ values well above the cut-off threshold

EXAMPLE 2

Case Studies of Flavour Profiles

The second example shows use of the methods of the present invention to process and evaluate data from a sample of considerable complexity. This example shows an embodiment comprising a multivariate analysis ("MVA") approach to MS data handling, two case studies are described. In the first, the present invention is used to perform principal component analysis ("PCA") on complex samples. In this approach, samples are compared by determining a correlation between chromatograms using a MVA based on the information content in the different masses detected by LC/MS analysis. Two-dimensional plots were made with spots representative for a given sample. In these plots, samples with similar information on similar masses are clustered together while more dissimilar samples are located at larger distances. These two-dimensional plots can be very effective as a means of pattern recognition for peptide/protein profiles.

As a second case study concerning multivariate analysis embodiments of the present invention, an application to GC/MS data is demonstrated. Complex flavor profiles were taken as a model in part because they can be analysed in great detail with respect to the identity of the compounds present and the intensity ratios between the compounds themselves. In the case of flavor profiles, MVA may be used to detect complex relations between compounds, for example, to unravel biochemical pathways. Moreover, MVA enables the selective detection of peaks with relevance to the trends and differences observed. The loading plots are useful for visualizing and determining these differences. These loading plots have been applied to a study on the formation of flavor compounds in fermented meat products (sausage batters) induced by two bacterial strains and their corresponding cell free enzymic extracts.

As described above, in one embodiment, a correlation is determined between a chromatogram processed according to the present invention and the chromatograms of one or more data sets, which may have also been processed according to the present invention. The correlation may be determined, for example, between mass chromatograms, IQ spectra, TIC chromatograms and RIC chromatograms. In this example, multivariate analysis was used to determine correlations. In cases in which very similar samples of considerable complexity have to be rapidly screened and the differences from chromatogram to chromatogram have to be recognized, MVA according to the present invention can speed up data evaluation. The need for rapid analysis of complex and similar samples is very often the real situation in the pharmaceutical and biotechnology industry, and will be more and more a problem to face in research fields like proteomics and body fluid profiling.

Figure 8:
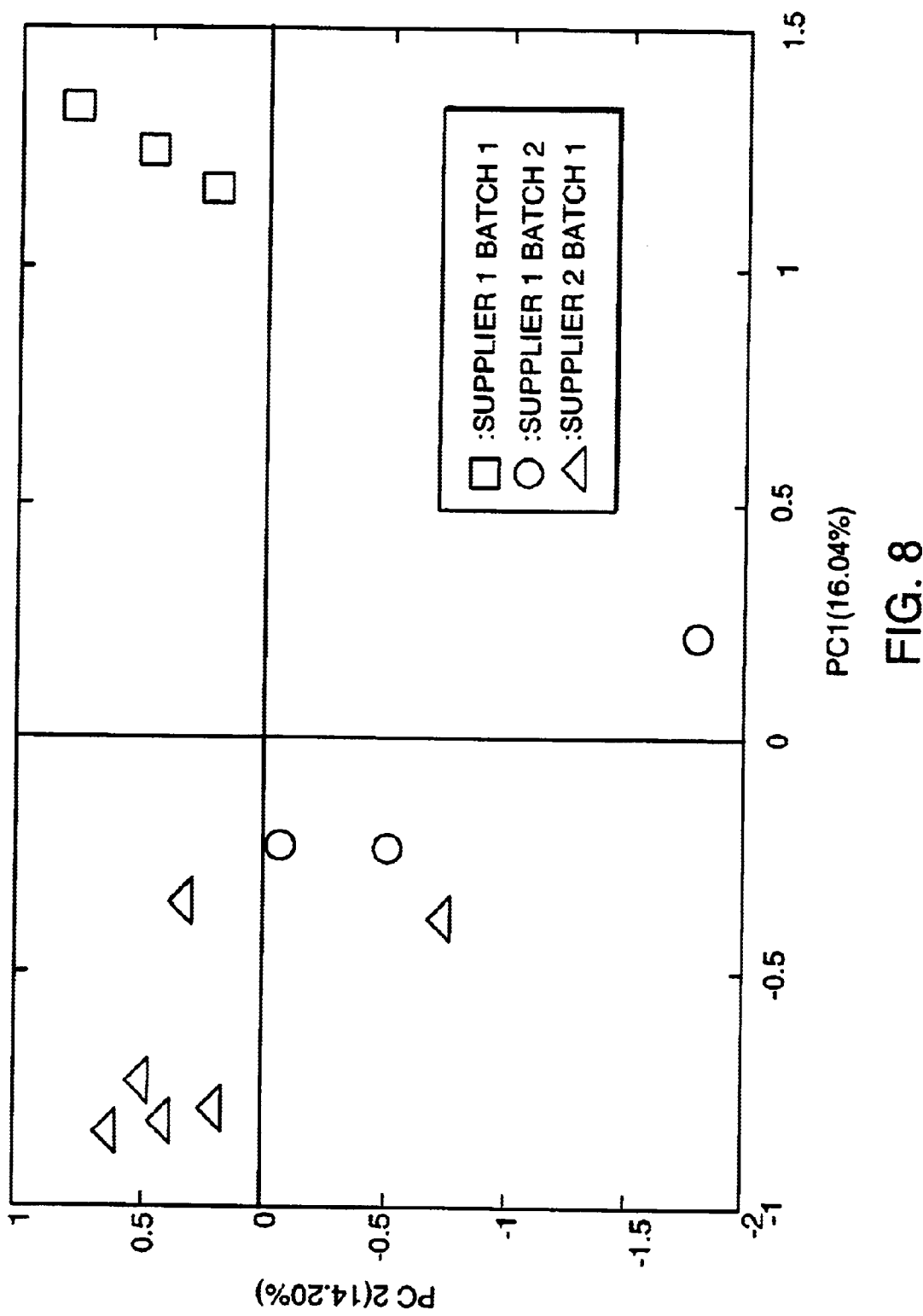
FIG. 8 shows a score plot for a set of three different BSA digests according to Example 2.

To evaluate pattern recognition on a biological sample, two BSA batches from one supplier and a third batch from another supplier were reduced, carbamidomethylated, digested and analysed by LC/MS as described above. The datafiles were subjected to principal component analysis (PCA) to determine a correlation between the IQ spectra. As can be seen in FIG. 8, the entire dataset corresponding to a LC/MS run is shown on the score plot as a point. The three slightly differing samples were concentrated in three different areas of the score plot, indicating that a pattern recognition approach could be applied to this particular class of LC/MS data. Evaluation of the loading plots further revealed differences between the batches and provided a quality evaluation criterium.

Figure 9C:
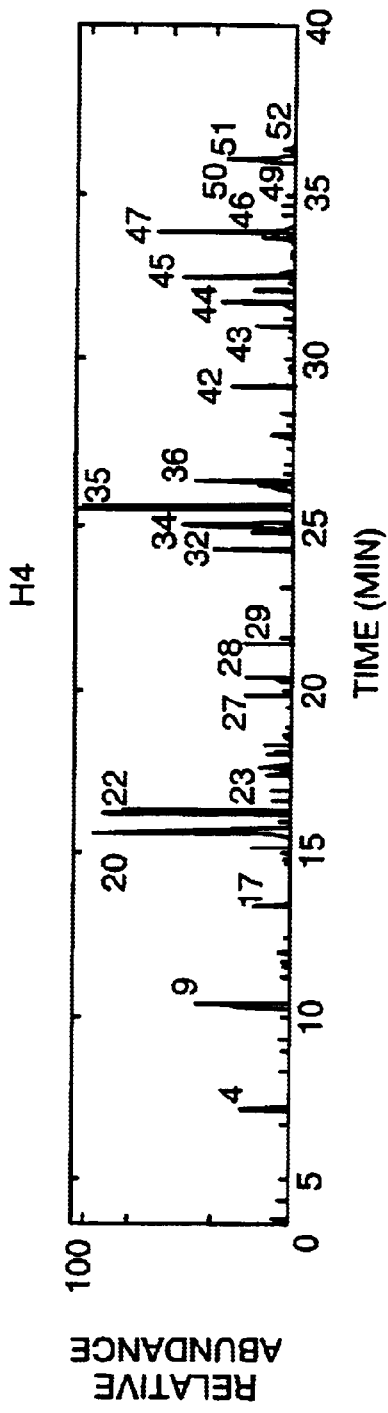
Figure 9D:
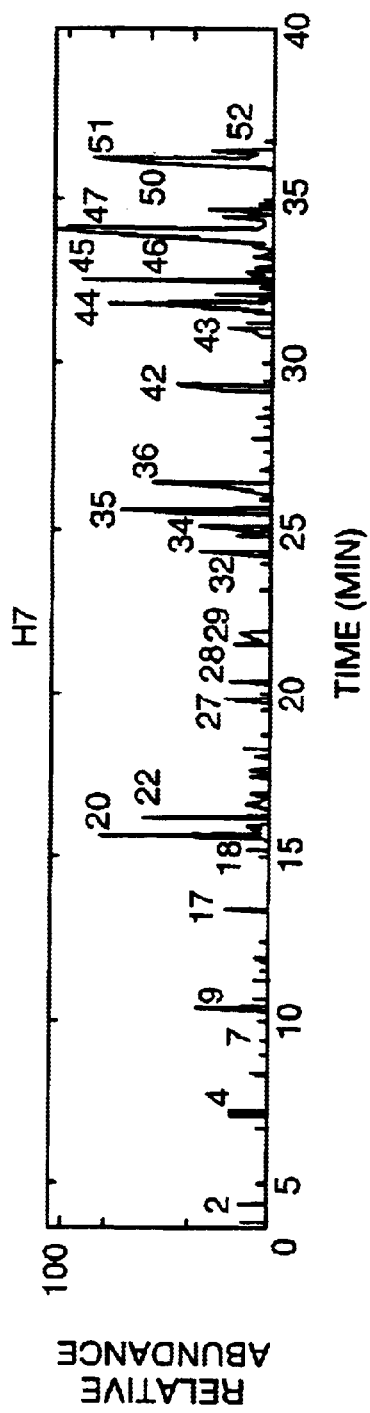

FIGS. 9A–D show examples of GC/MS TIC chromatograms of the fermentation experiments identified as H (see also Table 1) in which Lactobacillus, *Staphylococcus carnosus* and *Staphyllococcus carnosus* cell free extract were applied. FIG. 9A shows the chromatogram of experiment E0, batter before inoculation, or control batter (see also Table 1). FIGS. 9B–9D show, respectively, TIC chromatograms of the inoculations of experiments H2, H4 and H7. In the TIC chromatograms of the experiments E0, H2, H4 and H7, a strong increase in concentration of hexadecanal (peak 45), octadecanal (peak 49) and the higher fatty acids tetradecanoic acid, hexadecenoic acid, hexadecanoic acid, octadecadienoic acid, oleic acid and octadecanoic acid was observed during fermentation (FIGS. 9A–D; peaks 44, 46, 47, 50, 51 and 52, respectively). However, a second major effect was visible: increasing concentrations of small aldehydes and fatty acids. This effect was observed early during fermentation (FIG. 9B) for the peaks 4 (pentanal), 9 (hexanal), 32 (decenal), 34 (decadienal), 35 (decadienal isomer) and 36 (decanoic acid). These shorter chain oxidation products were absent in the control experiment (FIG. 9A).

Figure 10:
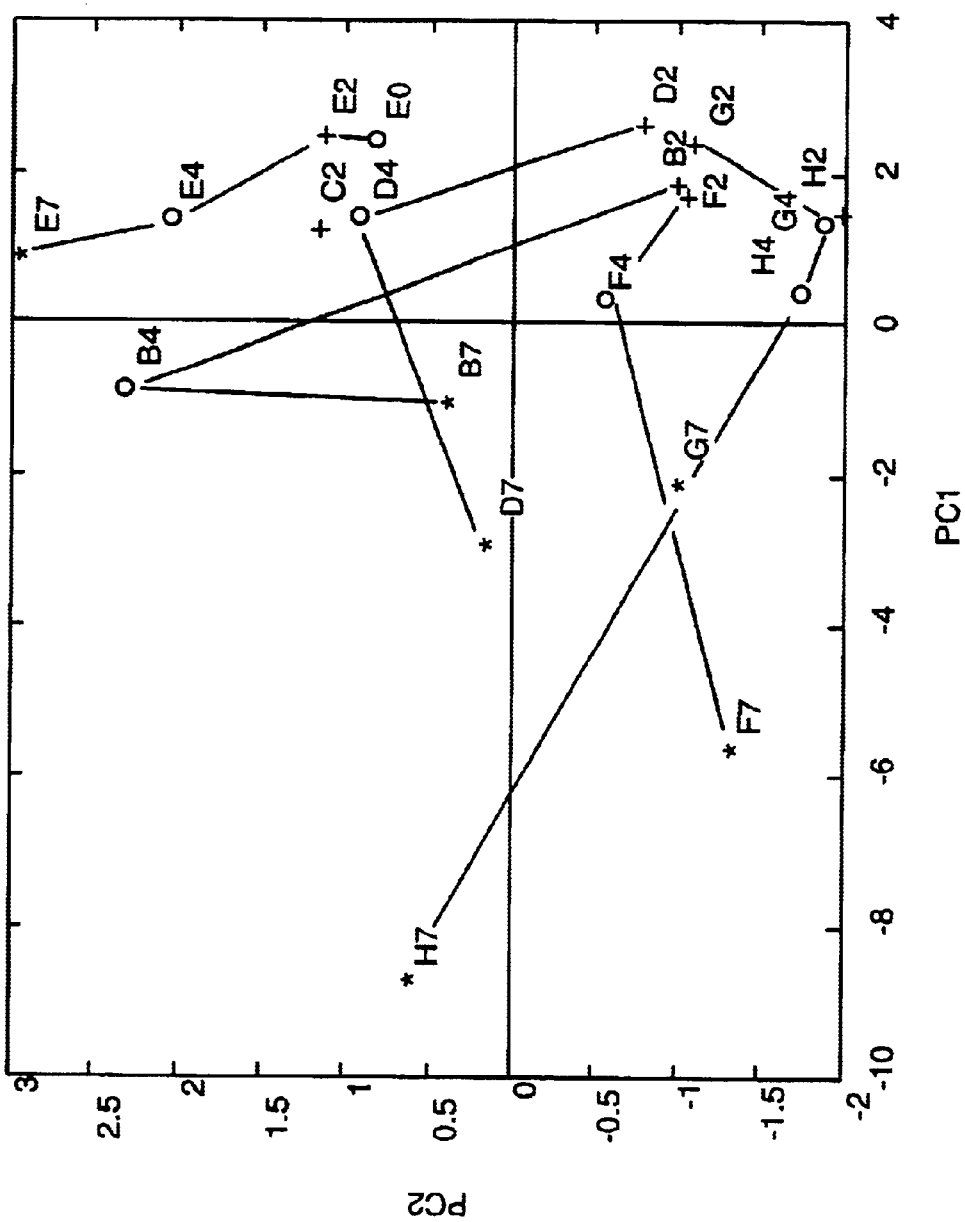
FIG. 10 shows a score plot PC1 vs. PC2 according to Example 2.
Figure 11A:
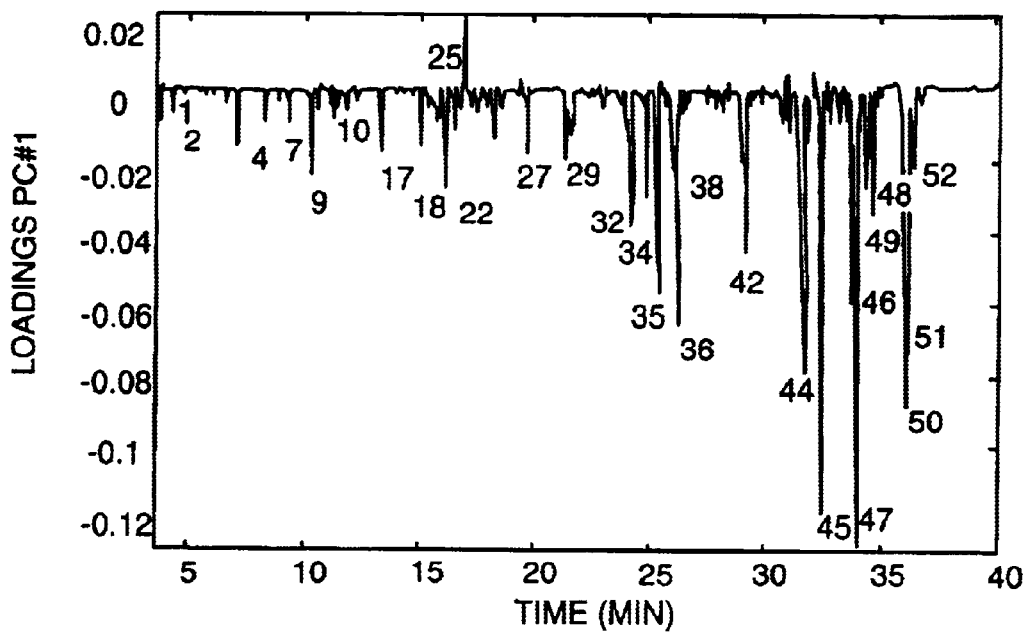
FIGS. 11A and 11B show loading plots for PC1 and PC2 according to Example 2.
Figure 11B:
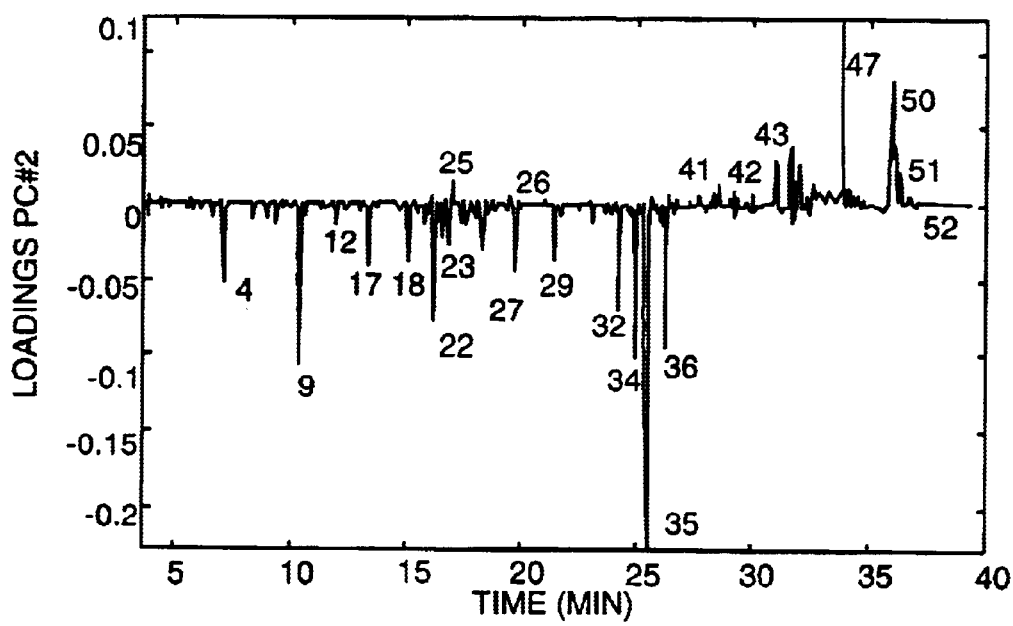

Principal component analysis (PCA) was applied using all time points (i.e., mass spectra) of the TIC chromatograms, and correlations were determined between the TIC chromatograms. This resulted in score plots and detailed loading plots. Differences in the formation of flavor compounds during ripening induced by the bacterial strains and enzymic mixtures applied were monitored using these plots. The score plot (PC1 vs. PC2, FIG. 10) presents a survey of the main trends occurring during fermentation. The corresponding chromatographic loading patterns of PC1 and PC2 are given in FIGS. 11A and 11B, respectively. Spectra of the control experiment (points labeled E0, E2, E4 and E7) showed a shift in a different direction compared to that of the inoculation experiments (B,D,F,G and H labeled data points). Moreover, a smaller shift occurred, indicating smaller changes in chemical composition.

The experiments with added bacteria generally showed an increase in the concentration of lower aldehydes and fatty acids. This tendency is mainly represented by the shift along PC 2, which is the dominant axis for short chain aldehydes and acids. The strong increase in concentration of the longer chain aldehydes and acids is almost exclusively represented by PC1. Although a general trend for the experiments of Table 1 with added strains and cell free extract is visible, especially for the experiments identified as F (with Lactobacillus and *Staphylococcus carnosus*) and those identified as H (with Lactobacillus, *Staphylococcus carnosus* and cell free extracts of *Staphylococcus Carnosus*), the formation of high concentrations of long chain aldehydes and fatty acids during the last phase of the fermentation (F7 and H7) is reflected in the score plot of FIG. 10. This example illustrates the effective processing and evaluation of complex chromatographic-mass spectrometric data by practice of the present invention.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

What is claimed is:

1. A method of data processing and evaluation comprising the steps of:
    (a) correcting the data points of a chromatogram for baseline to provide a corrected-chromatogram;
    (b) smoothing the data points of the chromatogram to provide a smoothed-corrected-chromatogram; and
    (c) determining an entropy value for the smoothed-corrected-chromatogram based on the product of a data point value and a logarithm of the data point value for a plurality of data points of the smoothed-corrected-chromatogram.

2. The method of claim 1, wherein the entropy value of a smoothed-corrected-chromatogram is defined substantially by $$H = \sum_{i/=0}^{n} p_i \ln(p_i),$$

where H is the entropy value, and $p_i$ is the intensity value of the $i^{th}$ data point of the smoothed-corrected-chromatogram.

3. The method of claim 2, further comprising the steps of:
    repeating steps (a) to (c) for a plurality of chromatograms of a data set; and
    determining a quality factor for a smoothed-corrected-chromatogram based on the entropy values of the plurality of chromatograms of the data set, the quality factor defined substantially by $$IQ = 1 - (H/H_{max}),$$

where IQ is the quality factor, H is the entropy value of the smoothed-corrected-chromatogram, and $H_{max}$ is the maximum entropy value of the plurality of chromatograms of the data set.

4. The method of claim 3 further comprising the step of generating a reconstructed total ion current chromatogram from a plurality of smoothed-corrected-chromatograms selected based on the quality factor of the individual smoothed-corrected-chromatograms.

5. The method of claim 4 further comprising the step of:
    assigning a mass signal quality value to each of one or more mass signals based on the difference between data points values corresponding to a mass signal before steps (a) and (b) and data points values corresponding to a mass signal after steps (a) and (b),
    wherein the step of generating a reconstructed total ion current chromatogram comprises excluding from the reconstructed total ion current chromatogram one or more mass signals selected based on the mass signal quality value of the individual mass signals.

6. The method of claim 1, further comprising the step of assigning a mass signal quality value to each of one or more mass signals based on the difference between data points values corresponding to a mass signal before steps (a) and (b) and data points values corresponding to a mass signal after steps (a) and (b).

7. The method of claim 6, further comprising the step of determining a correlation between each of a plurality of chromatograms of a data set and a smoothed-corrected-chromatogram associated with one or more mass signals selected based on the mass signal quality value of the individual mass signals.

8. The method of claim 7 wherein the step of determining a correlation comprises performing a multivariate analysis of the chromatograms of the data set with respect to the smoothed-corrected-chromatogram associated with one or more mass signals selected based on the mass signal quality value of the individual mass signals.

9. The method of claim 1 wherein the step of smoothing comprises use of a methodology substantially defined by a Savitsky-Golay algorithm.

10. A method of data processing and evaluation comprising the steps of:
    (a) correcting the data points of a chromatogram for baseline to provide a corrected-chromatogram;

(b) smoothing the data points of the chromatogram to provide a smoothed-corrected-chromatogram; and (c) determining an entropy value for the smoothed-corrected-chromatogram based on the product of a data point value and a logarithm of the data point value for a plurality of data points of the smoothed-corrected-chromatogram;

(d) repeating steps (a) to (c) for a plurality of chromatograms of a data set;

(e) determining a quality factor for a smoothed-corrected-chromatogram based on the entropy values of a plurality of chromatograms of the data set;

(f) assigning a mass signal quality value to each of one or more mass signals based on the difference between data points values corresponding to a mass signal before steps (a) and (b) and data points values corresponding to a mass signal after steps (a) and (b);

(g) determining a correlation between each of a plurality of chromatograms of a data set and a smoothed-corrected-chromatogram associated with one or more mass signals selected based on the mass signal quality value of the individual mass signals.

11. The method of claim 10 wherein the step of determining a correlation comprises performing a multivariate analysis of the chromatograms of the data set with respect to the smoothed-corrected-chromatogram associated with one or more mass signals selected based on the mass signal quality value of the individual mass signals.

* * * * *

UNITED STATES PATENT AND TRADEMARK OFFICE
CERTIFICATE OF CORRECTION

PATENT NO. : 6,743,364 B2
DATED : June 1, 2004
INVENTOR(S) : van der Greef et al.

It is certified that error appears in the above-identified patent and that said Letters Patent is hereby corrected as shown below:

Column 14,
Lines 7-10, replace "i1=□" with -- i =1 --.

Signed and Sealed this

Twenty-third Day of November, 2004

JON W. DUDAS
*Director of the United States Patent and Trademark Office*

UNITED STATES PATENT AND TRADEMARK OFFICE
CERTIFICATE OF CORRECTION

PATENT NO. : 6,743,364 B2
DATED : June 1, 2004
INVENTOR(S) : van der Greef et al.

It is certified that error appears in the above-identified patent and that said Letters Patent is hereby corrected as shown below:

Title page,
Item [75], Inventors, replace "Inventors: Jan van der Greef, Driebergen-Rijsenburg (NL)" with -- Inventors: Jan van der Greef, Driebergen-Rijsenburg (NL); Jacibus Thomas Wilhelmus, Elisabeth Vogels, Utrecht (NL); Florian Wulfert, Driebergen-Rijsenburg (NL); Albert Tas, Lienden (NL) --.

Signed and Sealed this

Tenth Day of May, 2005

JON W. DUDAS
*Director of the United States Patent and Trademark Office*